（12）United States Patent
Ringsred et al.

(10) Patent No.: US 9,174,035 B2
(45) Date of Patent: Nov. 3, 2015

(54) MICRONEEDLE ARRAY APPLICATOR AND RETAINER

(75) Inventors: Ted K. Ringsred, Minneapolis, MN (US); Franklyn L. Frederickson, White Bear Lake, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 726 days.

(21) Appl. No.: 11/718,461

(22) PCT Filed: Nov. 18, 2005

(86) PCT No.: PCT/US2005/041870
§ 371 (c)(1),
(2), (4) Date: May 2, 2007

(87) PCT Pub. No.: WO2006/055802
PCT Pub. Date: May 26, 2006

(65) Prior Publication Data
US 2008/0009825 A1    Jan. 10, 2008

Related U.S. Application Data

(60) Provisional application No. 60/629,143, filed on Nov. 18, 2004.

(51) Int. Cl.
*A61M 37/00* (2006.01)
*A61M 25/02* (2006.01)

(52) U.S. Cl.
CPC ..... *A61M 37/0015* (2013.01); *A61M 2025/026* (2013.01); *A61M 2025/0253* (2013.01); *A61M 2037/0023* (2013.01)

(58) Field of Classification Search
CPC .............. A61M 37/0015; A61M 2037/0023
USPC ......... 604/179, 272, 308, 174, 264, 181, 244, 604/116, 117, 118, 130, 131, 134, 136, 156, 604/157, 173, 177, 187, 191, 200, 258, 48, 604/73, 80, 93.01, 95.01, 46, 47, 95.02, 604/95.03, 95.04; 606/182, 183
See application file for complete search history.

(56) References Cited

U.S. PATENT DOCUMENTS 3,034,507 A    5/1962  McConnell et al.
3,072,122 A    1/1963  Rosenthal
(Continued)

FOREIGN PATENT DOCUMENTS

EP    407063    1/1991
GB    1080986   8/1967
(Continued)

OTHER PUBLICATIONS

U.S. Appl. No. 60/578,651, filed Jun. 10, 2004, Frederickson et al.
(Continued)

*Primary Examiner* — Kevin C Sirmons
*Assistant Examiner* — Shefali Patel (57) ABSTRACT

An applicator that has an elastic band to snap a microneedle array against skin with a predetermined force and velocity. The microneedle array, which may be pre-loaded with drug(s), is attached to the elastic band such that the band can be secured in place (e.g., wrapped around a person's arm), pulled away from the arm, and released from a suitable distance so that the microneedle array snaps back against the arm with sufficient force to cause an intended amount of penetration of microneedles. Also, a microneedle application device has an elastic band, a microneedle device, and a structure attaching the band to the microneedle device.

6 Claims, 11 Drawing Sheets

(56) References Cited

U.S. PATENT DOCUMENTS

| | | | |
|---|---|---|---|
| 3,123,212 A | 3/1964 | Taylor et al. | |
| 3,136,314 A | 6/1964 | Kravitz | |
| RE25,637 E | 9/1964 | Kravitz et al. | |
| 3,221,740 A | 12/1965 | Rosenthal | |
| 3,246,647 A | 4/1966 | Taylor et al. | |
| 3,322,121 A | 5/1967 | Banker | |
| 3,466,131 A | 9/1969 | Arcudi | |
| 3,510,933 A | 5/1970 | Taylor et al. | |
| 3,512,520 A | 5/1970 | Cowan | |
| 3,596,660 A | 8/1971 | Melone | |
| 3,675,766 A | 7/1972 | Rosenthal | |
| 3,678,150 A | 7/1972 | Szumski et al. | |
| 3,688,764 A | 9/1972 | Reed et al. | |
| 3,905,371 A | 9/1975 | Stickl et al. | |
| 3,908,356 A * | 9/1975 | Williams | G04B 37/1493 368/280 |
| 3,964,482 A | 6/1976 | Gerstel et al. | |
| 4,109,655 A | 8/1978 | Chacornac | |
| 4,237,906 A | 12/1980 | Havstad et al. | |
| 4,304,241 A | 12/1981 | Brennan | |
| 4,360,016 A | 11/1982 | Sarrine | |
| 4,453,926 A | 6/1984 | Galy | |
| 4,474,751 A | 10/1984 | Haslam et al. | |
| 4,503,856 A | 3/1985 | Cornell et al. | |
| 4,517,978 A | 5/1985 | Levin et al. | |
| 4,637,403 A | 1/1987 | Garcia et al. | |
| 4,858,607 A | 8/1989 | Jordan et al. | |
| 4,869,249 A | 9/1989 | Crossman et al. | |
| 4,920,977 A | 5/1990 | Haynes | |
| 4,924,879 A | 5/1990 | O'Brien | |
| 5,192,535 A | 3/1993 | Davis et al. | |
| 5,250,023 A | 10/1993 | Lee et al. | |
| 5,279,544 A * | 1/1994 | Gross et al. | 604/20 |
| 5,318,584 A | 6/1994 | Lange et al. | |
| 5,340,572 A | 8/1994 | Patel et al. | |
| 5,368,047 A | 11/1994 | Suzuki et al. | |
| 5,402,798 A | 4/1995 | Swierczek et al. | |
| 5,487,726 A | 1/1996 | Rabenau et al. | |
| 5,611,806 A | 3/1997 | Jang | |
| 5,639,000 A * | 6/1997 | McDaniel et al. | 224/175 |
| 5,879,326 A | 3/1999 | Godshall et al. | |
| 5,983,136 A | 11/1999 | Kamen | |
| 6,050,988 A | 4/2000 | Zuck | |
| 6,091,975 A | 7/2000 | Daddona et al. | |
| 6,132,755 A | 10/2000 | Eicher et al. | |
| 6,219,574 B1 | 4/2001 | Cormier et al. | 604/20 |
| 6,256,533 B1 | 7/2001 | Yuzhakov et al. | |
| 6,293,925 B1 | 9/2001 | Safabash et al. | |
| 6,313,612 B1 | 11/2001 | Honda et al. | |
| 6,322,808 B1 | 11/2001 | Trautman et al. | |
| 6,334,856 B1 | 1/2002 | Allen et al. | |
| 6,349,229 B1 * | 2/2002 | Watanabe et al. | 600/345 |
| 6,440,096 B1 | 8/2002 | Lastovich et al. | |
| 6,454,755 B1 | 9/2002 | Godshall | |
| 6,503,231 B1 | 1/2003 | Prausnitz et al. | |
| 6,532,386 B2 | 3/2003 | Sun et al. | |
| 6,537,242 B1 * | 3/2003 | Palmer | 604/22 |
| 6,589,202 B1 | 7/2003 | Powell | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,623,457 B1 | 9/2003 | Rosenberg | |
| 6,656,147 B1 | 12/2003 | Gertsek et al. | |
| 6,713,291 B2 | 3/2004 | King et al. | |
| 6,743,211 B1 | 6/2004 | Prausnitz et al. | |
| 6,797,276 B1 | 9/2004 | Glenn et al. | |
| 6,855,131 B2 | 2/2005 | Trautman et al. | |
| 6,881,203 B2 | 4/2005 | Delmore et al. | |
| 6,881,538 B1 | 4/2005 | Haddad et al. | |
| 6,890,319 B1 | 5/2005 | Crocker | |
| 6,908,453 B2 | 6/2005 | Fleming et al. | |
| 6,931,277 B1 | 8/2005 | Yuzhakov et al. | |
| 7,131,951 B2 * | 11/2006 | Angel | 600/567 |
| 2002/0032415 A1 | 3/2002 | Trautman et al. | |
| 2002/0082543 A1 | 6/2002 | Park et al. | |
| 2002/0087182 A1 | 7/2002 | Trautman et al. | |
| 2002/0091357 A1 | 7/2002 | Trautman et al. | |
| 2002/0095134 A1 | 7/2002 | Pettis et al. | |
| 2002/0111600 A1 | 8/2002 | Cormier et al. | |
| 2002/0123675 A1 | 9/2002 | Trautman et al. | |
| 2002/0138049 A1 | 9/2002 | Allen et al. | |
| 2002/0169416 A1 | 11/2002 | Gonnelli et al. | |
| 2002/0177858 A1 | 11/2002 | Sherman et al. | |
| 2002/0188245 A1 | 12/2002 | Martin et al. | |
| 2002/0198509 A1 | 12/2002 | Mikszta et al. | |
| 2003/0045837 A1 | 3/2003 | Delmore et al. | |
| 2003/0050602 A1 | 3/2003 | Pettis et al. | |
| 2003/0083641 A1 | 5/2003 | Angel et al. | |
| 2003/0135158 A1 | 7/2003 | Gonnelli | |
| 2003/0135161 A1 | 7/2003 | Fleming et al. | |
| 2003/0181863 A1 | 9/2003 | Ackley et al. | |
| 2003/0187395 A1 * | 10/2003 | Gabel et al. | A61M 5/14248 604/134 |
| 2003/0199812 A1 | 10/2003 | Rosenberg | |
| 2003/0208167 A1 * | 11/2003 | Prausnitz et al. | 604/272 |
| 2004/0049150 A1 | 3/2004 | Dalton et al. | |
| 2004/0077994 A1 | 4/2004 | Lastovich et al. | |
| 2004/0138612 A1 | 7/2004 | Shermer et al. | |
| 2004/0176732 A1 | 9/2004 | Frazier et al. | |
| 2004/0181203 A1 | 9/2004 | Cormier et al. | |
| 2005/0025778 A1 | 2/2005 | Cormier et al. | |
| 2005/0027242 A1 | 2/2005 | Gabel et al. | |
| 2005/0065463 A1 | 3/2005 | Tobinaga et al. | |
| 2005/0065466 A1 | 3/2005 | Vedrine | |
| 2005/0065472 A1 | 3/2005 | Cindrich et al. | |
| 2005/0096586 A1 | 5/2005 | Trautman et al. | |
| 2005/0106226 A1 | 5/2005 | Cormier et al. | |
| 2005/0137525 A1 | 6/2005 | Wang et al. | |
| 2005/0261631 A1 | 11/2005 | Clarke et al. | |

FOREIGN PATENT DOCUMENTS

| | | |
|---|---|---|
| GB | 2064329 | 6/1981 |
| GB | 2221394 | 2/1990 |
| WO | WO 96/10630 | 4/1996 |
| WO | WO 00/74766 | 12/2000 |
| WO | WO 01/36037 | 5/2001 |
| WO | WO 03084597 A1 * | 10/2003 |
| WO | WO 2005/051455 | 6/2005 |
| WO | WO 2005/051476 | 6/2005 |
| WO | WO 2005/065765 | 7/2005 |
| WO | WO 2005/082596 | 9/2005 |

OTHER PUBLICATIONS

Daddona Current Opinion in Drug Discovery and Development 1999 2(2);168-171.
Kaushik et al. Anesthesia Analg., 2001, 92, 502-504.
Henry et al. J. Pharm.Sci., 1998, 87,8,922-925.
McAllister et al. (1) Annual Review of Biomedical Engineering, 2000, 2, 289-313.
McAllister et al. (2) Proceed. Int'l. Symp. Control Release of Bioactive Material, 26, (1999), CRS, 192-193.

* cited by examiner

MICRONEEDLE ARRAY APPLICATOR AND RETAINER

CROSS-REFERENCE TO RELATED APPLICATIONS

This application is a national stage filing under 35 U.S.C. 371 of PCT/US2005/041870 filed Nov. 18, 2005, which claims priority to 60/629,143, filed Nov. 18, 2004, the disclosure of which is incorporated by reference in its/their entirety herein.

FIELD

The present invention relates to applicators used to apply microneedle arrays to a mammal. The present method also relates to methods of applying a microneedle array or patch to a mammal.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Issues related to applying microneedles include the ability to effectively insert the needles to a desired depth in the skin and the ability to protect the delicate microneedles prior to application to the skin.

SUMMARY OF THE INVENTION

In one embodiment, an applicator is provided that uses an elastic band to snap a microneedle array against the skin. This can be done with a predetermined force and velocity as needed e.g. with a handle connected directly or indirectly to the elastic band and a released system that releases the band at a predetermined level of stored energy. The microneedle array, which may be pre-loaded with drug(s), is attached to the elastic band such that the band can be secured in place (e.g., wrapped partially or entirely around a person's arm), pulled away from the arm, and released from a suitable distance so that the microneedle array snaps back against the arm with sufficient force to cause the intended amount of penetration of the microneedles. Such device can be easy to handle, simple to use, reliable, low cost, and suitable for inclusion in a disposable device. It also allows, if desired, to have the microneedle array held conveniently in place against the skin after application for an extended time period without the need for adhesives or the like.

In another embodiment, a break-away pull-tab may be used to pull the elastic and microneedle away from the skin. The tab can be calibrated so that it will break and release the microneedle array at a particular pull force. This may achieve a predetermined consistent force and velocity of application, which in turn may achieve a consistent insertion of the microneedles into the skin.

To avoid damage to and/or unintended penetration of the microneedles prior to intended application, a cover, spacer, or other protective shield may be put in place to keep the microneedles from being damaged prior to the time that they are actually inserted into the skin. For example, if the elastic band and microneedle array are first wrapped onto the arm it may be desired to have a cover that can be removed after the elastic band has been stretched. The shield can then be moved away when the elastic band and microneedle array are pulled away from the skin. The shield can be removed manually at that time or can be associated with a break-away mechanism so that it is automatically removed in conjunction with the pull and release action.

An alternative embodiment is to have the microneedle array remain in place against the skin, and then have the elastic band, optionally with a mass attached, pulled away and snapped against the back of the microneedle unit to cause insertion of the needles into the skin.

In another embodiment, the invention is a microneedle application device comprising an elastic band, and a microneedle device, wherein the microneedle device is attached to the elastic band.

In another embodiment, the invention is a method for applying a microneedle device comprising providing an elastic band attached to a housing and a gripping member. The housing is placed adjacent to a body appendage having a skin surface and the microneedle device is placed in proximity to the skin surface and the elastic band. The elastic band is stretched and released, such that the microneedle device is accelerated into the skin surface, thereby inserting at least a portion of the microneedles of the microneedle device into the skin surface.

As used herein, certain terms will be understood to have the meaning set forth below:

"Array" refers to the medical devices described herein that include one or more structures capable of piercing the stratum corneum to facilitate the transdermal delivery of therapeutic agents or the sampling of fluids through or to the skin.

"Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers may be used throughout the figures to denote like parts.

DETAILED DESCRIPTION

Figures 1, 2A:
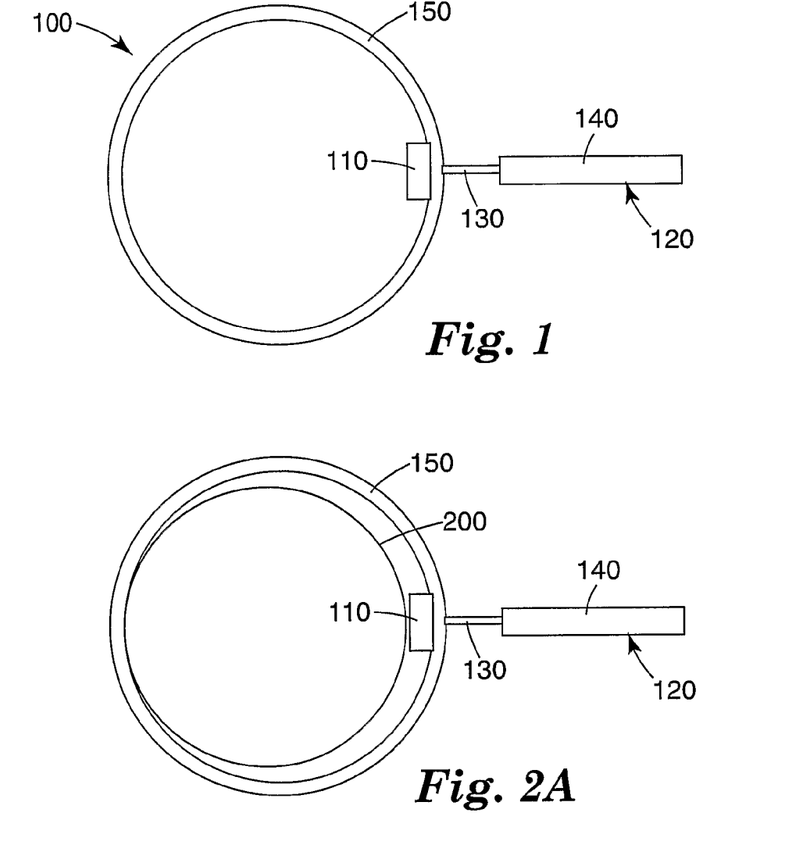
FIG. 1 is a schematic cross-sectional view of a microneedle application device.
FIG. 2A is a schematic cross-sectional view of a microneedle application device placed on an arm prior to insertion of the microneedle device.
Figure 2B:
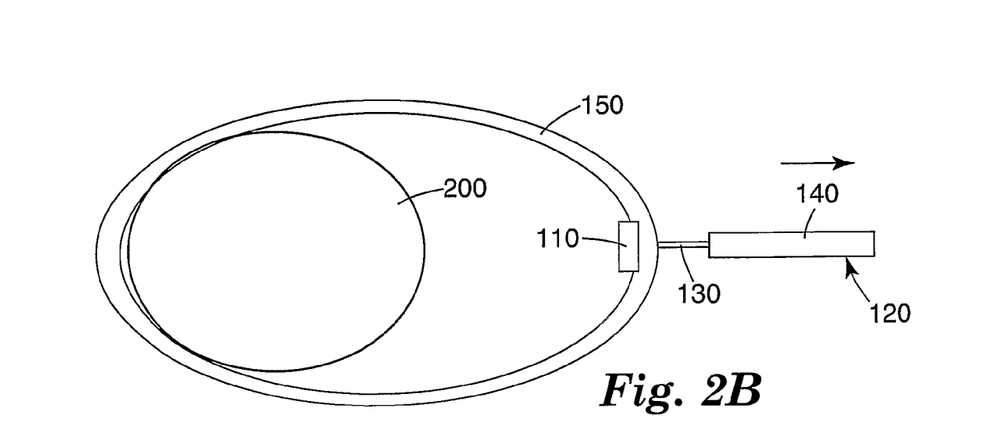
FIG. 2B is a schematic cross-sectional view of a microneedle application device in a stretched position during application and prior to detachment of the handle from the band.

One embodiment of the microneedle application device is shown in FIG. 1. The application device 100 comprises an elastic band 150, a microneedle device 110, a handle 120 which comprises a gripping member 140 and a connecting member 130. Use of the application device is shown in FIGS. 2A-E. In FIG. 2A, the application device 100 is shown having been placed on an arm 200 prior to insertion of the microneedle device 110 into the skin. In FIG. 2B, the application device is shown having been stretched so that the microneedle device 110 is pulled away from the skin surface. At a predetermined level of force or level of extension, which may for instance, be just larger than that shown in FIG. 2B, the connecting member 130 detaches from the elastic band 150, thereby allowing the band to snap back towards the arm (shown in FIG. 2C). The microneedle device 110 subsequently impacts the skin surface and the microneedles are inserted into the skin when the elastic band 150 has relaxed to conform to the arm (shown in FIG. 2D). The elastic band 150 may then be subsequently detached from the microneedle device 110, thereby leaving the microneedle device 110 in place on the skin (shown in FIG. 2E).

Figure 2C:
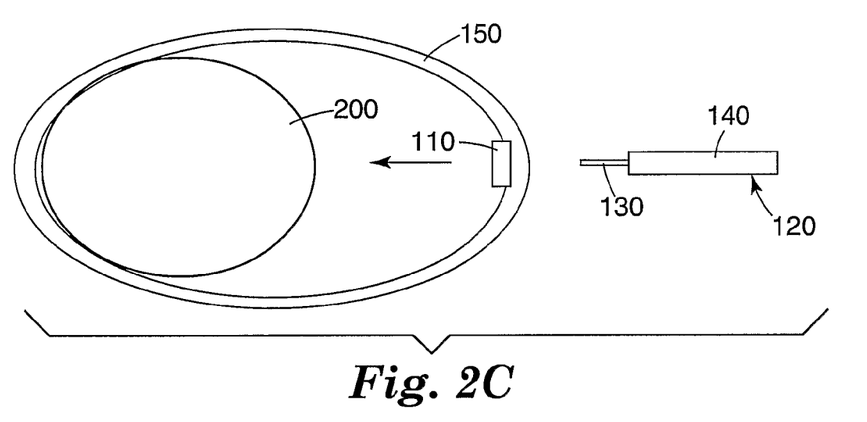
FIG. 2C is a schematic cross-sectional view of a microneedle application device snapping back to an arm subsequent to detachment of the handle from the band.
Figure 2D:
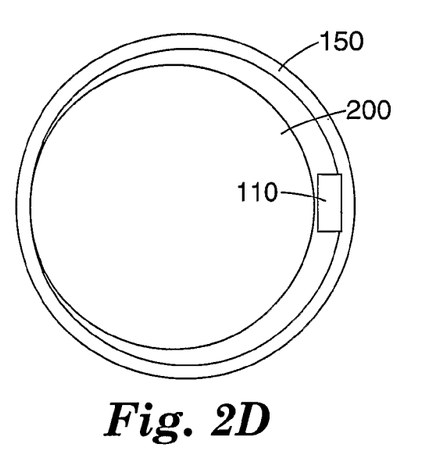
FIG. 2D is a schematic cross-sectional view of a microneedle application device that has impacted and been inserted into the skin.
Figure 2E:
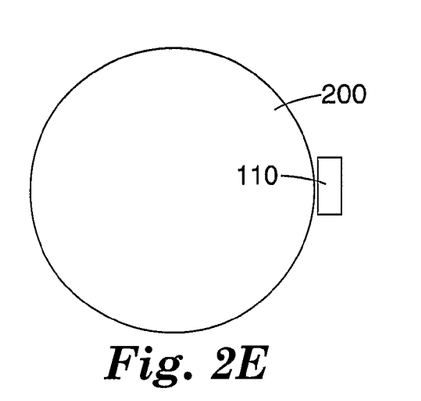
FIG. 2E is a schematic cross-sectional view of a microneedle device left in place on the skin after removal of the elastic band.

As depicted in FIG. 2C, the connecting member 130 detaches from the elastic band 150. In another embodiment, the connecting member 130 may remain attached to the elastic band 150 and instead become detached from the gripping member 140. In another embodiment, the connecting member 130 may also be configured so that it breaks into two or more pieces so that the gripping member is released from the elastic band and microneedle device. In this case, a portion of one end of the connecting member may remain attached to the elastic band 150 and a portion of the other end of the connecting member may remain attached to the gripping member 140. Other means of connecting or attaching the band to the microneedle device are also suitable, such as a thin perforated member that preferentially breaks at the perforation or a weak area of bonding the connecting member to either the band or the gripping member. Other suitable methods include releasable attachment connections, such as a repositionable adhesive, a hook and loop (e.g., Velcro™) attachment, or magnetic attachment. Still other suitable release mechanisms use mechanical arrangements involving spring-biased and/or flexing members that disengage from a latch or hook at a given force.

As depicted in FIG. 2A, the connecting member 130 is a separate piece connected to the band and the gripping member. In another embodiment, the connecting member may be integrally formed with the band and/or gripping member, such as for instance, by a narrowing section of the gripping member adjacent to the band. Alternatively, the connecting member may be a projection extending from the band that is configured to allow for detachment at a given force. In still another embodiment, the handle and microneedle device may be formed as one integral piece around which the elastic band is molded. The connecting member may be a small section that passes through the elastic band. In this fashion, the microneedle device and handle may both be attached to the elastic band by this mechanical connection without any need for additional connection means, such as an adhesive. In a variation on the foregoing embodiment, the microneedle device may be constructed with a small central connection point to which the connecting member may be attached by, for instance, a snap-fit type connection. In such a manner, it may be particularly convenient to assemble the device by individually molding the microneedle device, the handle having a connecting member, and piercing the connecting member through the elastic band to attach to the microneedle device. In still another embodiment the handle may be integrally formed with the elastic band, for instance as an elastic portion extending outward from the band and having a perforated or otherwise weakened section that serves as the connecting member. In still another embodiment, the connecting member may form a snap-fit connection with the gripping member, where the snap-fit connection is designed to release at a controlled force.

Figure 4A:
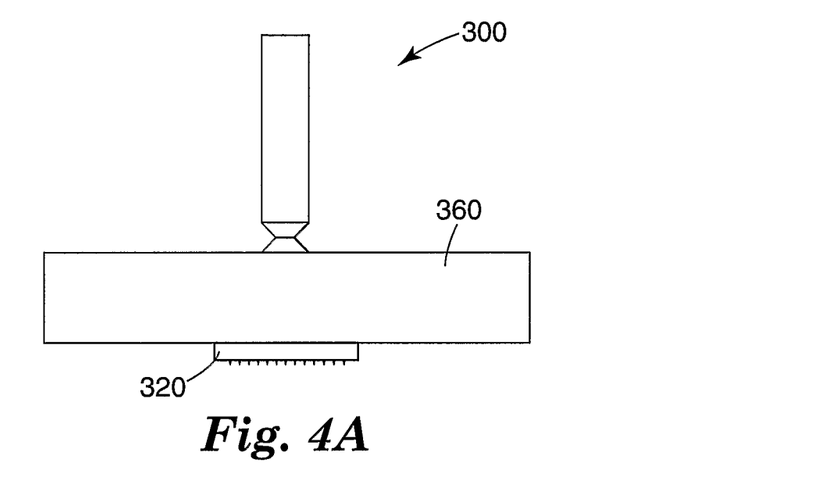
FIG. 4A is a schematic side view of one embodiment of a microneedle device.
Figure 4B:
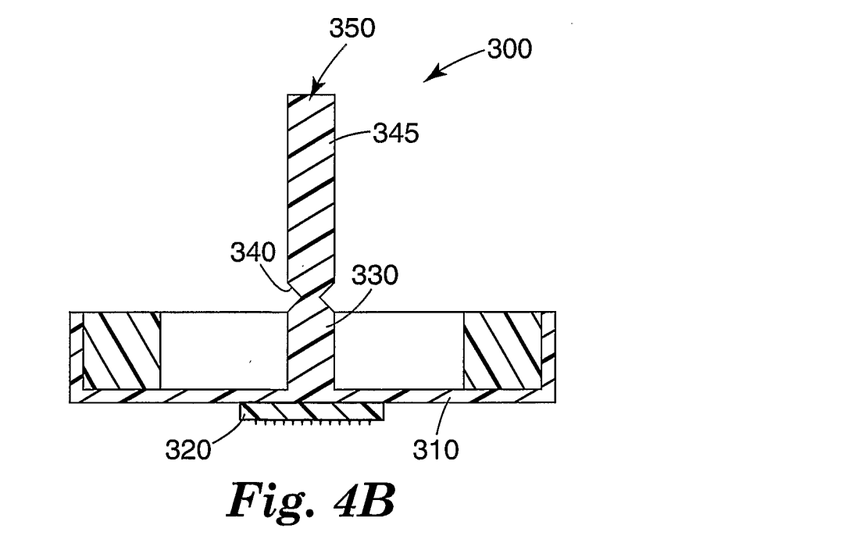
FIG. 4B is a schematic cross-sectional view of the microneedle device of FIG. 4A.
Figure 5:
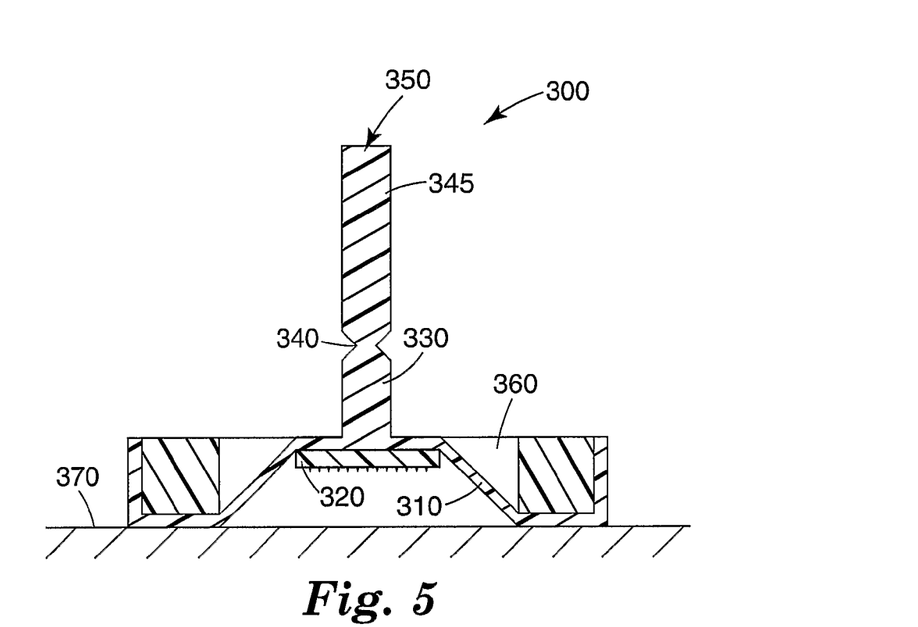
FIG. 5 is a schematic cross-sectional view of a microneedle device in a stretched position prior to detachment of the handle from the elastic band.
Figure 6:
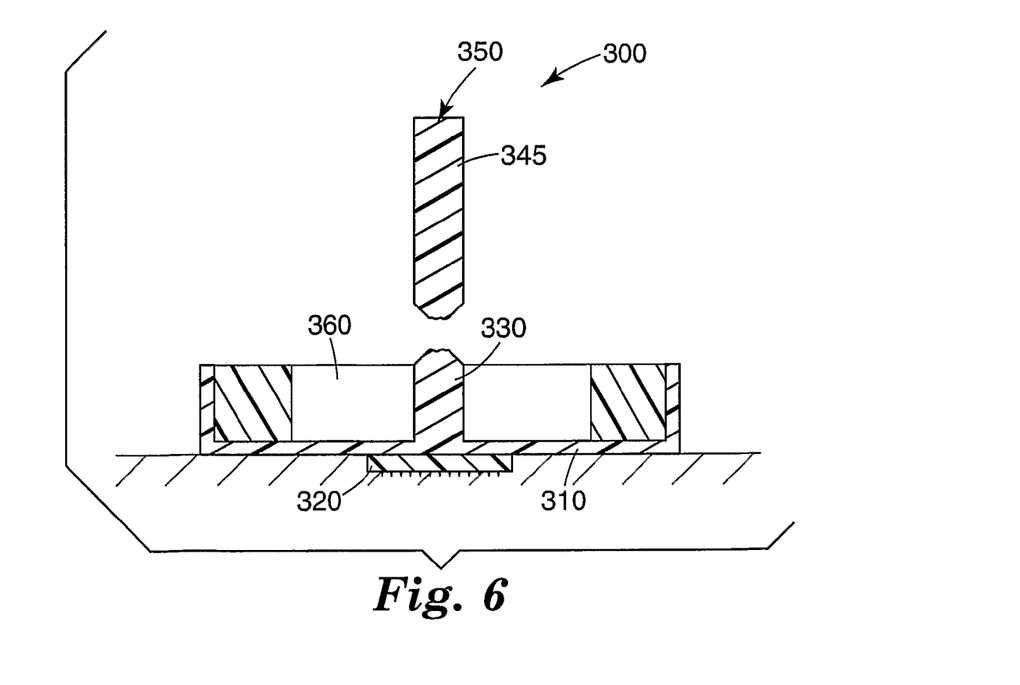
FIG. 6 is a schematic cross-sectional view of a microneedle array applied to a skin surface after the handle has been detached from the elastic band.

In another embodiment, the elastic band need not encircle an appendage. The device 300, shown in FIGS. 4A and 4B, has a microneedle array 320 attached to an elastic band 310. The elastic band 310 and/or array 320 is attached to a handle 350 which has a gripping member 345 and a connecting member 330. The handle 350 has a notch 340 at the connection between the gripping member 345 and the connecting member 330. The notch 340 is designed to allow the handle 350 to break when a controlled amount of force is applied to the handle 350. The elastic band 310 is held in place by a housing 360. The elastic band 310 shown in the cross-sectional view of FIG. 4B is affixed to the bottom and sides of the housing, but it may be connected to the housing by any other conventional means. As shown in FIG. 5, the device 300 has been placed and held against a skin surface 370 and the handle 350 is pulled upwards and away from the skin surface 370. As the handle 350 is pulled upwards, the band 310 is stretched. When a predetermined force is reached, the handle 350 breaks and the gripping member 345 is freed from the connecting member 330 at the notch 340, thus allowing the stretched elastic band 310 to accelerate the array 320 towards the skin 370. FIG. 6 shows the gripping member 345 detached from the connecting member 330, the elastic band 310 having recovered its initial, relaxed conformation, and the array 320 having been applied to the skin. The array 320 may be releasably attached to the band 310, in which case the housing 360 and band 310 may be removed from the skin 370, leaving the array 320 in place. Alternatively, the housing 360 and band 310 may be left in place on the skin 370 as a protective covering for the array 320.

The top of the housing 360 may be optionally configured as a solid surface having a hole through which the connecting member may be drawn upwards. The hole may be sized so as to be small enough to prevent the elastic band 310 and array 320 from being drawn upwards beyond the top of the housing, thus serving as a stop or limiting mechanism determining the maximum extension of the elastic band 310. The amount of force needed to raise the array 320 and band 310 to the stop or limit mechanism is preferably less than the force needed to break the handle 350 from the remainder of the connecting member. Thus the band 310 may be stretched to a predetermined limit before further application of upward force to the handle breaks and releases the connecting member.

Figure 7A:
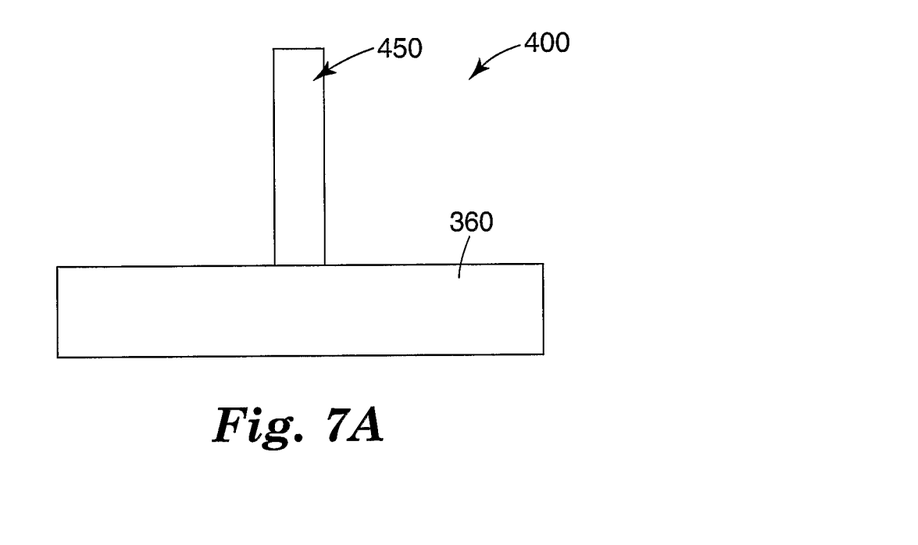
FIG. 7A is a schematic side view of another embodiment of a microneedle device.
Figure 7B:
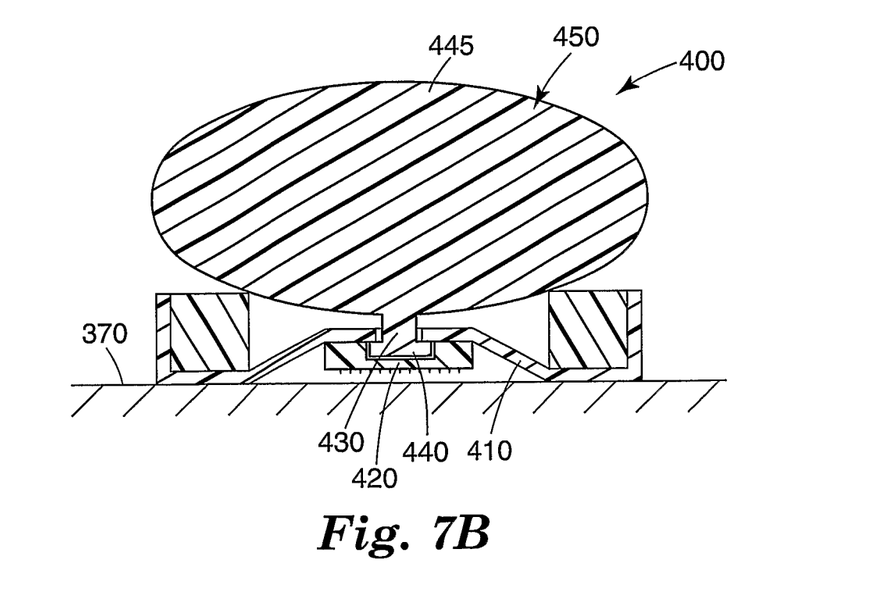
FIG. 7B is a schematic cross-sectional view of the microneedle device of FIG. 7A.
Figure 8A:
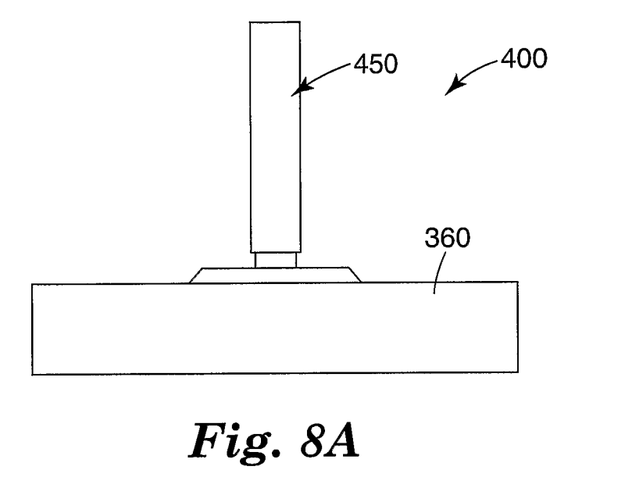
FIG. 8A is a schematic side view of the microneedle device of FIG. 7A in a stretched position just prior to detachment of the handle from the elastic band.
Figure 8B:
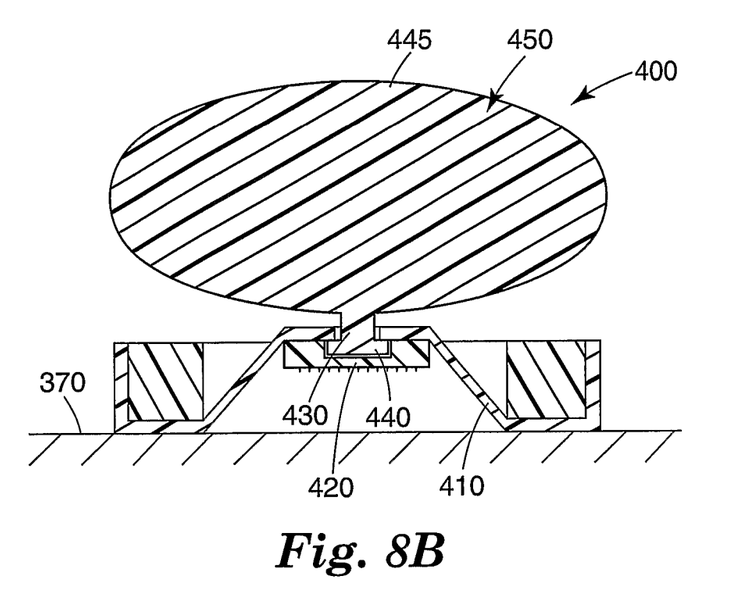
FIG. 8B is a schematic cross-sectional view of the microneedle device of FIG. 8A.
Figure 9A:
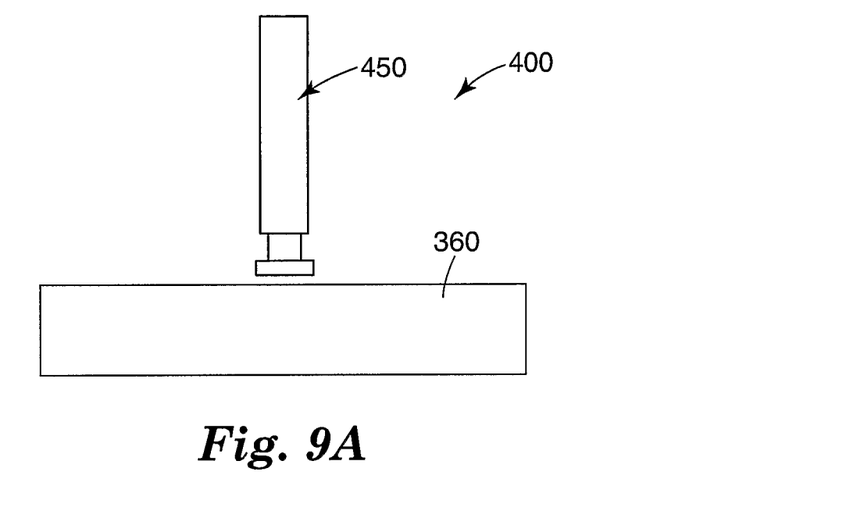
FIG. 9A is a schematic side view of the microneedle device after the handle has been detached from the elastic band and the array has been applied to the skin.
Figure 9B:
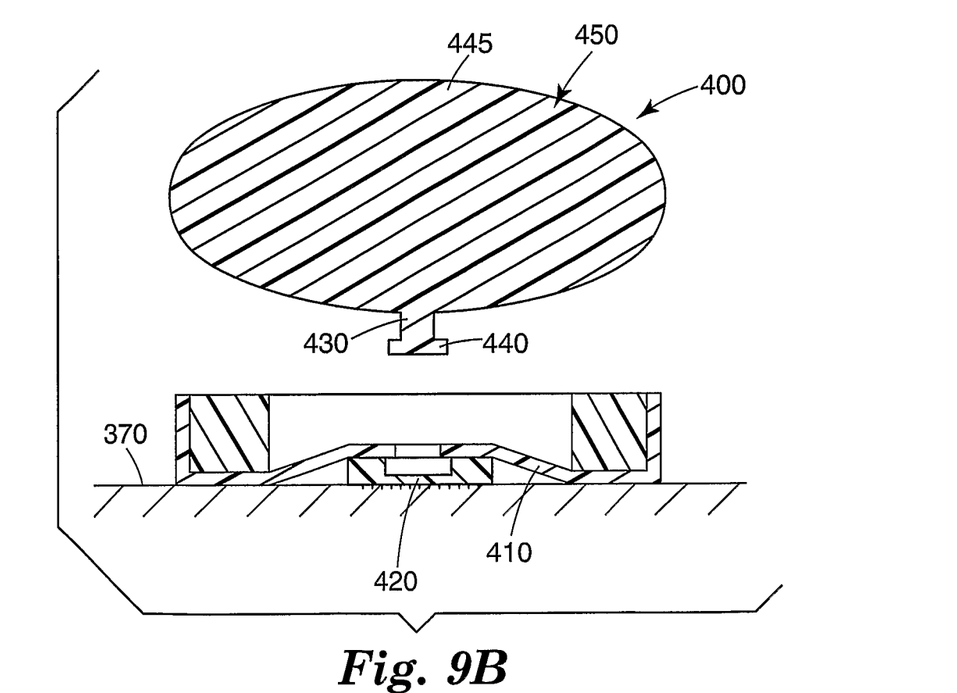
FIG. 9B is schematic cross-sectional view of the microneedle device of FIG. 9A.

In another embodiment, an alternative means of connecting the handle 450 to the array 420, as shown in FIGS. 7A and 7B, is employed. The handle 450 has an easily graspable, disk shaped gripping member 445 which is connected to the band 410 and array 420 by a connecting member 430 that terminates in a flange 440. The band 410 surrounds a portion of the connecting member 430 and holds the handle 450 adjacent to the array 420. The device 400 is shown in a partially activated or cocked state with the band 410 partially stretched away from the target, skin surface. The device 400 is shown at its maximum extension in FIGS. 8A and 8B. The downward force applied by the stretched band 410 is then large enough to cause the flange 440 to slide past the band 410, thereby detaching the handle 450 from the array 420, allowing the array 420 to be accelerated towards and make contact with the skin, as shown in FIGS. 9A and 9B.

Figure 10A:
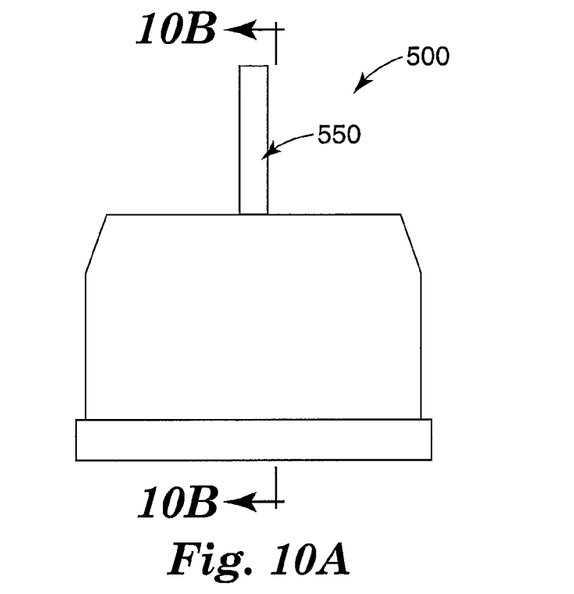
FIG. 10A is a schematic side view of another embodiment of a microneedle device.
Figure 10B:
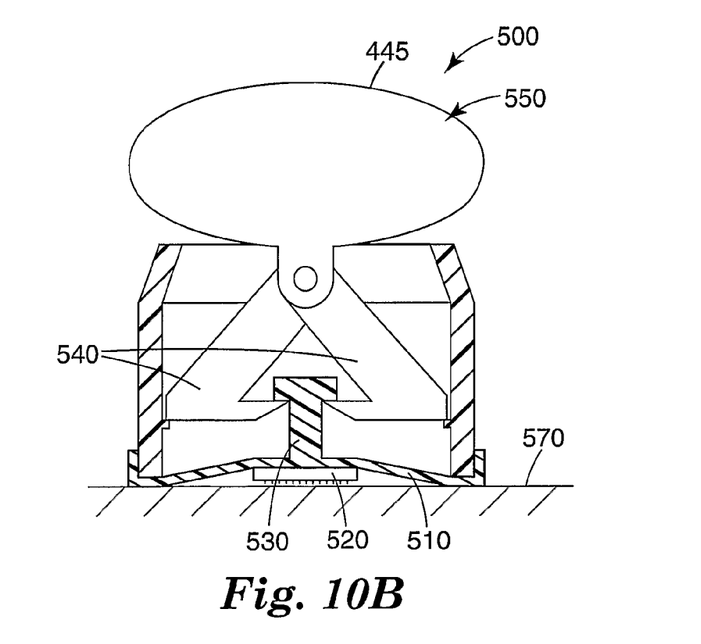
FIG. 10B is a schematic cross-sectional view of the microneedle device of FIG. 10A.
Figure 11A:
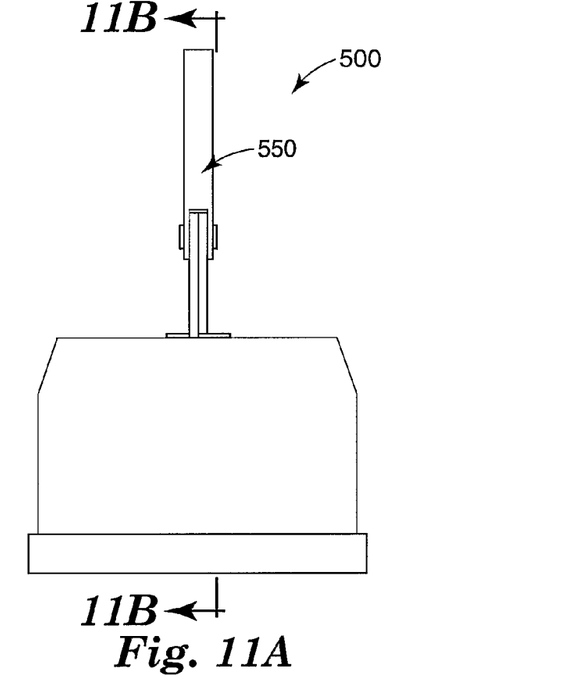
FIG. 11A is a schematic side view of the microneedle device of FIG. 10A in a stretched position just prior to detachment of the handle from the elastic band.
Figure 11B:
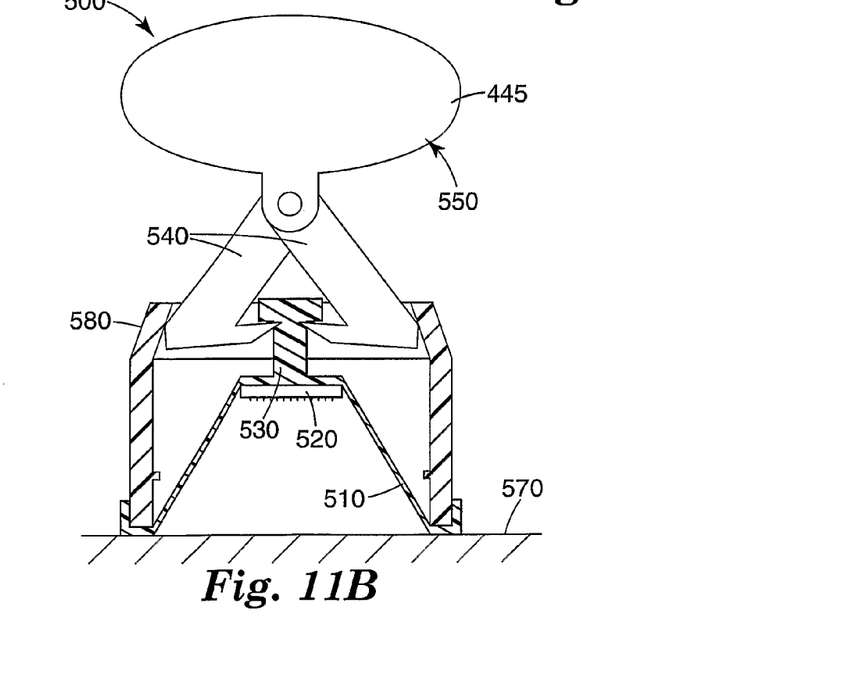
FIG. 11B is a schematic cross-sectional view of the microneedle device of FIG. 11A.
Figure 12A:
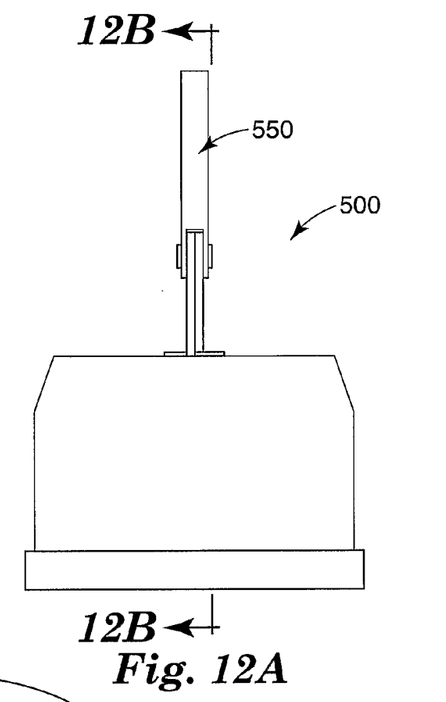
FIG. 12A is a schematic side view of the microneedle device of FIGS. 10 and 11 after the handle has been detached from the elastic band and the array has been applied to the skin.
Figure 12B:
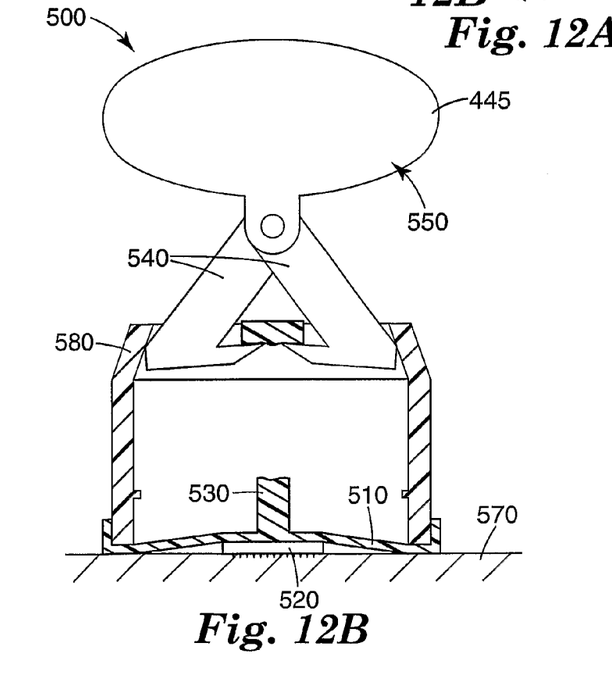
FIG. 12B is schematic cross-sectional view of the microneedle device of FIG. 12A.

In still another embodiment, the handle 550 may have a gripping member 445 that is attached to cutting members 540 that can grasp the connecting member 530, as shown in FIGS. 10A and 10B. As the handle 550 is drawn upwards the cutting members 540 are pressed towards each other by the tapered shape of the housing 580, as shown in FIGS. 11A and 11B. The cutting members 540 sever the connecting member 530, thereby allowing the elastic band 510 to accelerate the array 520 towards the skin 570 and causing the array 520 to make contact with the skin 570, as shown in FIGS. 12A and 12B. Any suitable mechanism may be used to perform the function of the cutting members, such as a scissors mechanism, sharp blades, or the like. As shown, two cutting members act in opposition, but the cutting function may be performed by a single blade moving across the connecting member 530 or by more than 2 blades acting together. A feature such as the notch shown in FIGS. 4 to 6 may be used in conjunction with cutting members to help align the leading edges of the cutting members and reduce the force needed to sever the connecting member.

In one embodiment, it may be desirable to allow the elastic band to be temporarily held in a partially or fully stretched orientation by a stop mechanism. For example, as shown in FIG. 7B, the gripping member 445 and the housing serve as a stop mechanism. The gripping member 445 contacts or interferes with the housing of the device at rest (i.e., as the device would be prepared during manufacture), thereby holding the elastic band 410 in a partially stretched state and keeping the microneedle array 420 in a recessed position from the exterior of the housing. This recessed position allows for maintenance of a protective distance between the microneedle array and the target surface prior to application, thus protecting the microneedle array from inadvertent damage by the user. Removal of the gripping member 445 during use will then allow the elastic band to press the microneedle array 420 against a target surface. Any number of suitable designs may be used to provide such a "pre-stretched" position. For example, the device shown in FIG. 10B has protrusions along the inner surface of the outer casing that combine with the cutting members to serve as a stop mechanism. The protrusions interfere with the cutting members and the device would be prepared in a pre-stretched state with the cutting members resting on the protrusions so as to keep the device in a partially stretched state prior to application.

Alternatively, the elastic band may be provided in a non-stretched state from the manufacturer and during storage, but may be partially or fully stretched by the user to a "cocked" position prior to placing the device on a target surface. In such an embodiment, the array may be protected during storage by a cover that is removed prior to application. Cocking of the device prior to use may be accomplished by any number of means known to one skilled in the art. For example, the type of device generally shown in FIGS. 10A-B could be optionally configured so that the elastic band would be flat, the array would protrude from the housing during storage, and the cutting members would initially be positioned just below the protrusions along the inside surface of the outer casing. As the gripping member 445 is lifted the cutting members 540 would be pressed inward by the protrusion and allowed to slip over the protrusion due to the sloping angle of the upper surface of the cutting member. The cutting members 540 would be prevented, however, from sliding downwards past the protrusion due to the interference between the square protrusion and the flat lower surface of the cutting member 540. Thus the device could be placed into a partially cocked position (as shown in FIG. 10B) by the user and held in place temporarily by the stop mechanism (i.e., interference between cutting members and protrusion). Further extension of the gripping member 445 would ultimately result in the cutting members 540 severing the connecting member 530 and allowing the microneedle array 520 to be deployed against a skin surface. In another example, the gripping member shown in FIGS. 7A-B could be configured so that it is free to rotate about the axis along which it is pulled. In the rest ("unstretched") state the gripping member could be aligned such that it does not interfere with the housing. The band could then be pulled upward to partially stretch the band and then rotated to a position where the gripping member would now interfere with the housing, thereby leaving the device in a cocked position (as shown in FIG. 7B). Pulling upward further on the gripping member would then detach the gripping member from the elastic band and allow the elastic band to press the microneedle array 420 against a target surface. Similar stop mechanisms, such as a ratchet, could be used, for example, where the detachable gripping member could be raised upwards and away from the device and prevented from recoiling due to interference with the ratchet. Detachment of the gripping member from the array would then allow the elastic band to press the array against a target surface.

It is desired that the elastic band be stretched to a predetermined force and/or extension before the connecting member releases the band and microneedle device. This allows for a consistent force of application when the array is impacted into the skin upon relaxation of the band. Delivery of a patch using a patch application device in accordance with the methods of the present invention may involve acceleration of the patch application device itself to a desired velocity.

A method of applying a microneedle device using an application device of the present invention involves having the microneedle device reach a desired velocity that is effective to pierce the microneedles into the skin. The desired velocity is preferably controlled to limit or prevent stimulation of the underlying nerve tissue. The maximum velocity achieved by the microneedle device upon impact with the skin is often 20 meters per second (m/s) or less, potentially 15 m/s or less, and possibly 10 m/s or less. In some instances, the maximum velocity be 8 m/s or less. In other instances, the minimum velocity achieved by the microneedle device upon impact with the skin is often 2 m/s or more, potentially 4 m/s or more, and possibly 6 m/s or more.

Because of the variability in the location of skin and the size of different individual's appendages, it is optional that the application device be designed such that the microneedle device travels at a velocity at or above the desired minimum velocities over a distance that is sufficient to accommodate the variations in skin location and appendage size relative to the application device. For example, the microneedle device in the application device may move at or above the minimum velocity over a distance of one millimeter or more. In some embodiments, the microneedle device may move at or above the minimum velocity over a distance of 5 millimeters or more.

The force required to reach the desired velocities may vary based on the mass of the microneedle device, the size of the appendage to which it is applied, and the size and shape of the elastic band. The mass of the microneedle device may be controlled or selected to reduce the likelihood that nerve tissue underneath the delivery site is stimulated sufficiently to result in the sensation of pain. For example, the mass of the microneedle device be about 6 grams or less, possibly about 4 grams or less. In some instances, it may be desirable to provide additional mass onto or around the area of releasable attachment between microneedle device and elastic band. This additional mass can provide additional force to aid in insertion of the microneedles into the skin.

The elastic band 150 may be constructed of any conventional rubber or elastomer. Examples of suitable materials include butadiene rubber, nitrile rubber, styrenic block copolymers, ethylene-propylene-diene (EPDM) rubber, silicone rubber, and natural rubber. It should be understood that the elastic band need not be in the shape of a conventional rubber band (i.e. a flat, narrow, cylindrically shaped layer of rubber). Any elastomeric or rubber member that may encircle a body part may be suitable for use as the elastic band of the present invention. Alternatively, the elastomeric or rubber member may be a flat layer of rubber that can be affixed to a housing. For example, such a flat layer may be in the shape of a rectangle, square, oval, or circle.

The gripping member may be constructed so that it is convenient for handling by a healthcare provider or patient. This may be for example, a flat tab that can be pinched between thumb and forefinger, a cylindrical section that may be easily gripped by a full hand, a ring attached by a string or wire to the elastic band, or any number of other equally suitable constructions readily apparent to one of skill in the art.

Figure 3:
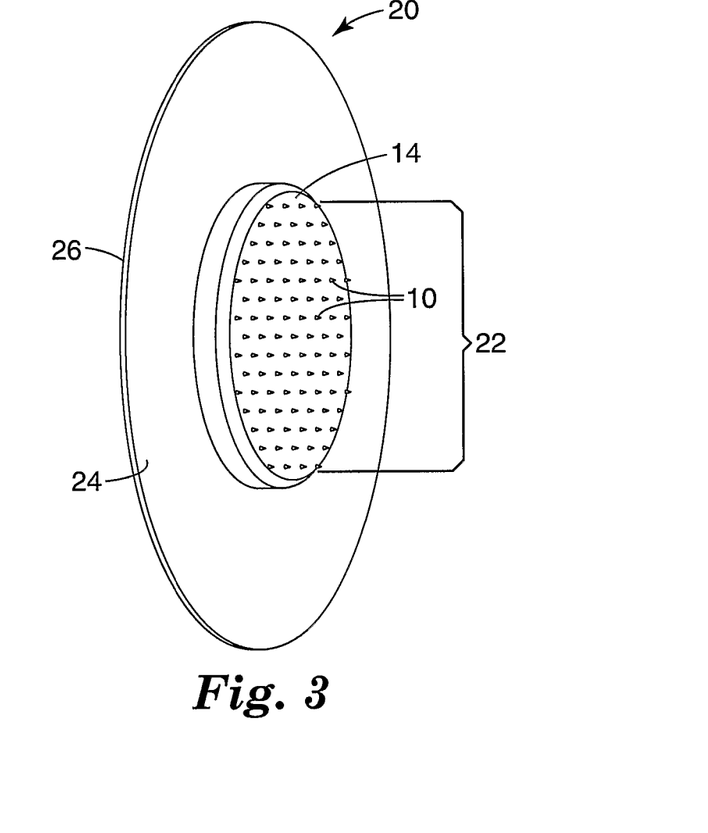
FIG. 3 is a schematic perspective view of a patch microneedle device.

In one embodiment, the microneedle device shown schematically as 110 in FIGS. 1 and 2 may be in the form of a patch shown in more detail in FIG. 3. FIG. 3 illustrates a microneedle device comprising a patch 20 in the form of a combination of an array 22, pressure sensitive adhesive 24 and backing 26. A portion of the array 22 is illustrated with microneedles 10 protruding from a microneedle substrate surface 14. The microneedles 10 may be arranged in any desired pattern or distributed over the microneedle substrate surface 14 randomly. As shown, the microneedles 10 are arranged in uniformly spaced rows. In one embodiment, arrays of the present invention have a distal-facing surface area of more than about 0.1 cm$^2$ and less than about 20 cm$^2$, preferably more than about 0.5 cm$^2$ and less than about 5 cm$^2$. In one embodiment (not shown), a portion of the substrate surface 14 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 cm$^2$) to less than about 1 square inch (6.5 cm$^2$). In another embodiment (shown in FIG. 3), the microneedles are disposed over substantially the entire surface area of the array 22.

The microneedle devices useful in the various embodiments of the invention may comprise any of a variety of configurations, such as those described in the following patents and patent applications, the disclosures of which are herein incorporated by reference. One embodiment for the microneedle devices comprises the structures disclosed in United States Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in co-pending U.S. patent application, Ser. No. 10/621620 filed on Jul. 17, 2003 which describes microneedles having a truncated tapered shape and a controlled aspect ratio. Still another embodiment for the microneedle devices comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,313,612 (Sherman, et al.) which describes tapered structures having a hollow central channel. Still another embodiment for the micro arrays comprises the structures disclosed in International Publication No. WO 00/74766 (Gartstein, et al.) which describes hollow microneedles having at least one longitudinal blade at the top surface of tip of the microneedle.

Microneedle devices suitable for use in the present invention may be used to deliver drugs (including any pharmacological agent or agents) through the skin in a variation on transdermal delivery, or to the skin for intradermal or topical treatment, such as vaccination.

Microneedle devices of the present invention may be useful when applied to the skin as a "pretreatment" step, that is, when applied to the skin to disrupt the stratum corneum layer of skin and then removed. The disrupted area of skin may then be useful for allowing enhanced delivery of a solution or patch containing a pharmacological agent that is applied to the disrupted area. Microneedle devices of the present invention may also be useful when coated with a pharmacological agent that dissolves from the microneedles after they are inserted into the skin. Microneedle devices of the present invention may also be useful when provided with a fluid reservoir of pharmacological agent that can pass through one or more conduits in the device to be delivered into the skin after the microneedles are inserted into the skin.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing immune response of vaccine adjuvants. In one aspect, the drug may be applied to the skin (e.g., in the form of a solution that is swabbed on the skin surface or as a cream that is rubbed into the skin surface) prior to applying the microneedle device.

Microneedle devices may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

In one embodiment, the present invention is a method for applying a microneedle device comprising the following steps: providing an elastic band; placing the elastic band in circumferential proximity to a body appendage having a skin surface; placing a microneedle device in proximity to the skin surface and the elastic band; stretching the elastic band; and releasing the elastic band, such that the microneedle device is accelerated into the skin surface, thereby inserting at least a portion of the microneedles of the microneedle device into the skin surface. In one aspect the microneedle device is releasably attached to the elastic band prior to the step of stretching the elastic band. In one aspect it may be desired to remove the elastic band from circumferential proximity to the body appendage subsequent to the microneedles being inserted into the skin surface while leaving the microneedle device inserted into the skin surface.

In another embodiment, the microneedle device may be placed directly against the skin prior to the steps of stretching and releasing the elastic band, such that the elastic band impacts the microneedle device thereby inserting at least a portion of the microneedles of the microneedle device into the skin surface. It may be desirable to provide additional mass to the elastic band so as to provide sufficient force for impacting and pressing the microneedles into the skin.

In another embodiment, a handle is attached to the elastic band and the step of stretching the elastic band is effected by pulling on the handle.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A microneedle application device comprising:
    an elastic band configured so as to encircle an appendage having a skin surface, the elastic band stretchable to a stretched position;
    a microneedle device, wherein the microneedle device is attached to the elastic band;
    a handle releasably attached to the elastic band; and
    a release system,
    wherein when the band is in the stretched position, the release system releases the band from the handle at a predetermined level of stored energy such that the stretched band accelerates the microneedle device into the skin surface.

2. The microneedle application device according to claim 1 wherein the elastic band is releasably attached to the microneedle device.

3. The microneedle application device according to claim 1, wherein the handle is adapted to allow the band to be stretched.

4. The microneedle application device according to claim 3 wherein the handle comprises a connecting member connected to a gripping member, characterized in that the connecting member is detachable from the band.

5. The microneedle application device according to claim 4 wherein a predetermined force is required to detach the connecting member.

6. The microneedle application device according to claim 4 wherein the connecting member and the gripping member are integrally formed.

* * * * *

UNITED STATES PATENT AND TRADEMARK OFFICE
CERTIFICATE OF CORRECTION

PATENT NO. : 9,174,035 B2  
APPLICATION NO. : 11/718461  
DATED : November 3, 2015  
INVENTOR(S) : Ted Ringsred Page 1 of 1

It is certified that error appears in the above-identified patent and that said Letters Patent is hereby corrected as shown below:

Specification

<u>Column 1</u>
Line 46, Delete "e.g." and insert -- e.g., --, therefor.

<u>Column 1</u>
Line 47, Delete "released" and insert -- release --, therefor.

<u>Column 1</u>
Line 55, Delete "Such device" and insert -- Such a device --, therefor.

<u>Column 9</u>
Line 50, Delete "pamedronate;" and insert -- pamidronate; --, therefor.

Signed and Sealed this
Fifth Day of April, 2016

Michelle K. Lee
*Director of the United States Patent and Trademark Office*